(12) United States Patent
Wu et al.

(10) Patent No.: US 10,219,703 B2
(45) Date of Patent: Mar. 5, 2019

(54) METHOD AND SYSTEM FOR INTRA-ORAL IMAGINE USING HDR IMAGING AND HIGHLIGHT REMOVAL

(71) Applicant: Carestream Health, Inc., Rochester, NY (US)

(72) Inventors: Yingqian Wu, Shanghai (CN); Wei Wang, Shanghai (CN); Guijian Wang, Shanghai (CN); Victor C. Wong, Rochester, NY (US)

(73) Assignee: Carestream Dental Technology Topco Limited, London (GB)

( * ) Notice: Subject to any disclaimer, the term of this patent is extended or adjusted under 35 U.S.C. 154(b) by 0 days.

(21) Appl. No.: 15/021,279

(22) PCT Filed: Sep. 30, 2013

(86) PCT No.: PCT/CN2013/084691
§ 371 (c)(1),
(2) Date: Mar. 11, 2016

(87) PCT Pub. No.: WO2015/042939
PCT Pub. Date: Apr. 2, 2015

(65) Prior Publication Data
US 2016/0220118 A1 Aug. 4, 2016

(51) Int. Cl.
*A61B 5/00* (2006.01)
*A61C 9/00* (2006.01)
(Continued)

(52) U.S. Cl.
CPC .............. *A61B 5/0088* (2013.01); *A61B 1/24* (2013.01); *A61B 5/7225* (2013.01);
(Continued)

(58) Field of Classification Search
CPC ..................................................... A61B 5/0088
(Continued)

(56) References Cited

U.S. PATENT DOCUMENTS

| | | |
|---|---|---|
| 6,236,751 B1 | 5/2001 | Farrell |
| 7,084,868 B2 | 8/2006 | Farag et al. |

(Continued)

FOREIGN PATENT DOCUMENTS

| | | |
|---|---|---|
| CN | 101588750 A | 11/2009 |
| CN | 102509279 A | 6/2012 |

(Continued)

OTHER PUBLICATIONS

Yang, Q. et al. "Real-Time Specular Hhighlight Removal Using Bilateral Filtering", In: Daniilidis K., Maragos P., Paragios N. (eds) Computer Vision—ECCV 2010. ECCV 2010. Lecture Notes in Computer Science, vol. 6314. Springer, Berlin, Heidelberg.*

(Continued)

*Primary Examiner* — Allen Porter, Jr.

(57) ABSTRACT

A method and system for intra-oral imaging using High Dynamic Range (HDR) and highlight removal is presented. The method comprising generating a first High HDR irradiation map of teeth with multiple images captured with different exposures for same intra-oral scene; and removing highlight caused by a specular reflection in a detail-reserved way from the first HDR irradiation map so as to obtain a second HDR irradiation map in which the specular reflection is at least partly suppressed.

15 Claims, 3 Drawing Sheets

(51) Int. Cl.
*A61B 1/24* (2006.01)
*G06T 5/50* (2006.01)
*H04N 5/235* (2006.01)
*G06T 5/00* (2006.01)

(52) U.S. Cl.
CPC ............ *A61C 9/0053* (2013.01); *G06T 5/008* (2013.01); *G06T 5/50* (2013.01); *H04N 5/2355* (2013.01); *G06T 2207/20208* (2013.01); *G06T 2207/30036* (2013.01)

(58) Field of Classification Search
USPC ......................................................... 600/476
See application file for complete search history.

(56) References Cited

U.S. PATENT DOCUMENTS

| | | |
|---|---|---|
| 7,146,059 B1 | 12/2006 | Durand et al. |
| 8,218,963 B2 | 7/2012 | Adelsberger et al. |
| 8,224,045 B2 | 7/2012 | Burns et al. |
| 8,670,622 B2 | 3/2014 | Kono et al. |
| 2010/0268069 A1 | 10/2010 | Liang |
| 2011/0164811 A1 | 7/2011 | Ishiyama |
| 2012/0141029 A1 | 6/2012 | Cha et al. |
| 2012/0288217 A1 | 11/2012 | Zhai et al. |

FOREIGN PATENT DOCUMENTS

| | | |
|---|---|---|
| JP | H1155808 A | 6/1999 |
| JP | 2000115538 A | 9/1999 |
| JP | 2012073953 | 4/2012 |

OTHER PUBLICATIONS

Ciurescu, D. et al. "Digital Radiography using High Dynamic Range Technique".*

In: Mastorakis, Nikos. Mathematical methods and applied computing : proceedings of the Applied Computing Conference 2009 (ACC '09), proceedings of the 11th International Conference on Mathematical Methods and Computational Techniques in Electrical Engineering (MMACTEE '09), Vouliagmeni, Athens, Greece, Sep. 28-30, 2009.*

Salih, Y. et al. "Tone Mapping of HDR images: A Review". Abstract. 2012 4th International Conference on Intelligent and Advanced Systems (ICIAS2012) Intelligent and Advanced Systems (ICIAS), 2012 4th International Conference on. 1:368-373 Jun. 2012.*

International Search Report, International application No. PCT/CN2013/084691, dated Jun. 30, 2014, 2 pages.

Pawel Gorny, Department of Computer Graphics and Multimedia Systems, Szczecin Univ. of Technology, Highlight Removal Method for HDR Images, 2005, pp. 1-6.

Fredo Durand et al., Laboratory for Computer Science, Fast Bilateral Filtering for the Display of High-Dynamic-Range Images, 2002, pp. 1-10.

European Supplementary Search Report, Application No. EP 13 89 4795, dated Apr. 5, 2017, 2 pages.

Debevec, Paul E., et al., "Recovering High Dynamic Range Radiance Maps from Photographs", ACM SIGGRAPH 1997 Conference Proceedings pp. 369-378 (Debevec).

JP, 2nd Office Action, Notification of Reasons for Refusal with English translation, Patent Application Serial No. 2016-518700, dated May 22, 2018, 6 pages.

* cited by examiner

METHOD AND SYSTEM FOR INTRA-ORAL IMAGINE USING HDR IMAGING AND HIGHLIGHT REMOVAL

CROSS REFERENCE TO RELATED APPLICATIONS

This application claims the benefit of and is a U.S. National Phase filing of PCT Application PCT/CN2013/084691 filed Sep. 30, 2013, entitled "METHOD AND SYSTEM FOR INTRA-ORAL IMAGING USING HDR IMAGINE AND HIGHLIGHT REMOVAL", in the name of Wu et al, which is incorporated herein in its entirety.

FIELD OF THE INVENTION

The present application generally relates to a method and system for intra-oral imaging, particularly relates to use high dynamic range(HDR) imaging and highlight removal so as to remove specular reflection and obtain highly clear HDR image.

BACKGROUND

In dental field, it is important to obtain a teeth image during the course of treatment. An intra-oral camera can provide a convenience for directly imaging the teeth in the cavity environment, and it is widely used in hospitals.

However, since surfaces of teeth are very smooth and translucent, and covered with saliva, it is very easy to capture some specular reflection brought from the smooth surface. For both auto-exposure and fixed-exposure, the specular reflection would always result in some over-saturation highlight regions in the images, which greatly damages the details of the images and makes the images displayed ultimately very unclear for density. In certain dental practice, such as the examination of some amalgam areas and moisture tooth smooth surface, the over-saturated highlight regions make it impossible to make any diagnosis on lesions in reflection region and make visual observations very difficult.

More importantly, the over-saturated specular highlight regions caused by the specular reflection make any computer-based automatic lesions detection system fail in the regions, which will be regarded as false positive or false negative.

Although technology of HDR imaging has been widely used in the field of image processing, it is rarely applied to the field of 2D intra-oral imaging. Moreover, in certain cases, even if the intra-oral imaging technical solution adopting the technology of HDR, it can't suppress the aforesaid specular reflection and remove the over-saturated highlight area.

It would, therefore, be desirable to provide a method which remove the specular reflection such that highly clear images of teeth can be presented.

SUMMARY OF THE INVENTION

The present invention aims to address the problems described above.

According to one aspect of the invention, a method for intra-oral imaging is provided, and this method comprises the steps of:
generating a first High Dynamic Range (HDR) irradiation map of teeth with multiple images captured with different exposures for same intra-oral scene; and
removing highlight caused by a specular reflection in a detail-reserved way from the first HDR irradiation map so as to obtain a second HDR irradiation map in which the specular reflection is at least partly suppressed.

The method according to an embodiment of the present application, the step of generating the first HDR irradiation map includes steps of:
capturing the multiple images with different exposures for same intra-oral scene;
determining one image of the multiple images as key exposure frame;
recovering an irradiation mapping curve based on the multiple images; and
recovering the first HDR irradiation map based on the multiple images and the irradiation mapping curve, which includes steps of:
mapping the pixel value into irradiation value for every one of the multiple images based on the irradiation mapping curve, and
obtaining the first HDR irradiation map by weighted averaging the irradiation values of all of the multiple images for every pixel.

According to another aspect of the invention, a system for intra-oral imaging is provided, and this system comprises:
a HDR imaging device for generating a first High Dynamic Range (HDR) irradiation map of teeth with multiple images captured with different exposures for same intra-oral scene; and
a detail-reserved filter for removing highlight caused by a specular reflection from the first HDR irradiation map so as to obtain a second HDR irradiation map in which the specular reflection is at least partly suppressed.

According to yet another aspect of this invention, a method for suppressing the specular reflection is provided, and this method comprises the steps of:
generating a first High Dynamic Range (HDR) irradiation map of teeth with multiple images captured with different exposures for same intra-oral scene; and
removing highlight caused by a specular reflection in a detail-reserved way from the first HDR irradiation map so as to obtain a second HDR irradiation map in which the specular reflection is at least partly suppressed.

According to yet another aspect of this invention, a computer program product is provided, and the computer program product comprising a computer readable medium which including instructions for performing the following steps:
generating a first High Dynamic Range (HDR) irradiation map of teeth with multiple images captured with different exposures for same intra-oral scene; and
removing highlight caused by a specular reflection in a detail-reserved way from the first HDR irradiation map so as to obtain a second HDR irradiation map in which the specular reflection is at least partly suppressed.

BRIEF DESCRIPTION OF THE DRAWINGS

The above and other objects and advantages of the invention will become fully understood from the following detailed description with reference to drawings, in which identical or similar elements are denoted by identical reference signs.

DETAILED DESCRIPTION OF THE INVENTION

Some of the many possible embodiments of the invention will be described below in order to provide a basic understanding of the invention and not to identify crucial or decisive elements of the invention or define the scope of protection. It can be easily understood that according to the technical solutions of the invention, those with ordinary skills in the art can propose other alternative implementations without departing from the true spirit of the invention. Therefore, the following embodiments and accompanying drawings are illustrative description of technical solutions of the invention, and should not be construed as constituting the whole of the invention or as limiting or defining technical solutions of the invention.

Figure 1:
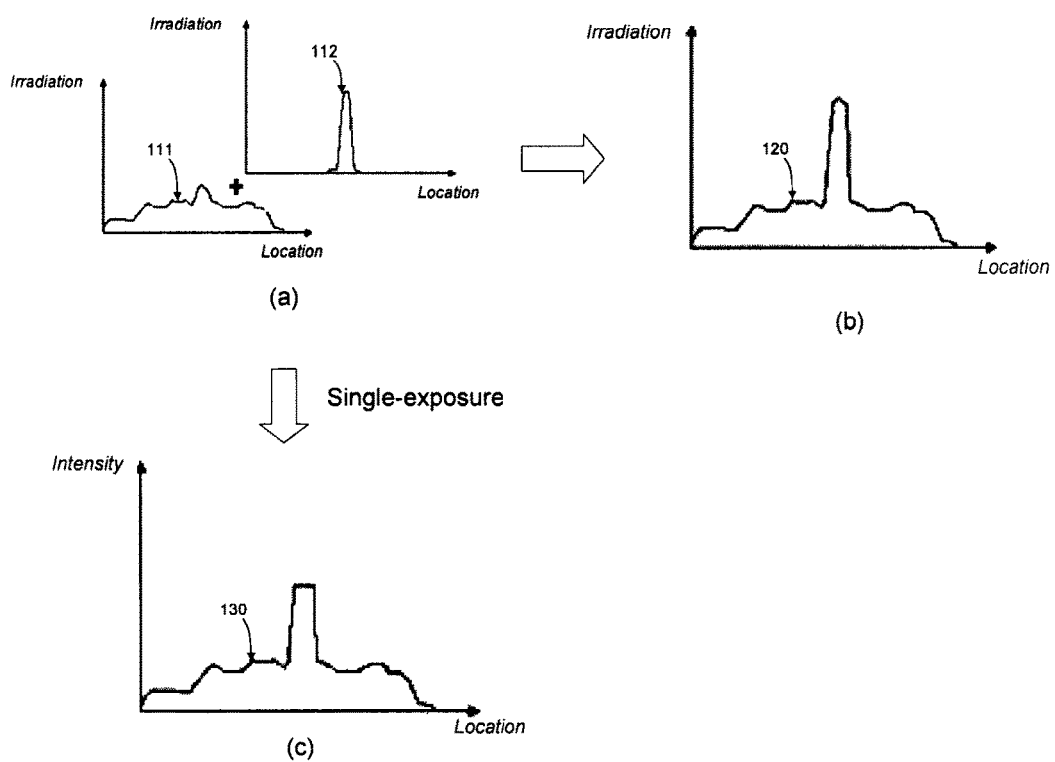
FIG. 1 shows a schematic diagram of single-exposure image with intra-oral camera in prior art.

FIG. 1 shows a schematic diagram of single-exposure image with intra-oral camera in prior art. The problems pointed out in the Background part of this application will be more clearly understood from the disclosure of FIG. 1. In particular, FIG. 1(a) shows diffuse reflection 111 and specular reflection 112 actually produced when a LED illuminated an intra-oral environment; FIG. 1(b) shows an original irradiation mapping 120 that represents an actual inputting irradiation of the intra-oral camera; FIG. 1(c) shows a displayed image radiation map 130 with low dynamic range obtained after a single-exposure. In the process of single-exposure imaging, the intra-oral camera can't completely capture the original irradiation mapping shown in FIG. 1(b).

Since there are some specular reflections for the intra-oral environment, the actual reflection from certain intra-oral scene can be decomposed as the diffusion reflection and the specular reflections as illustrated in FIG. 1(a). It is obvious that the irradiation value of the specular reelection is greater than that of the diffusion reflection, which makes range of intensity larger than that of the scene without specular reflection. Naturally, it produce a highlight region corresponding to the specular reflection that appears as a wave crest. Moreover, for a normal intra-oral camera, in case of single exposure, it only can generate an image with low dynamic image in which the intensity of the highlight region is in an over saturated state under while other regions corresponding to the diffusion reflection with low intensity are represented as under-exposed; thus, the image in FIG. 1(c) appears distorted and unclear.

For detail, in oral environment, smooth teeth surfaces, saliva, gum and other organic tissues occur together, and their emission and reflection of illumination, so-called irradiation, differ very much. Since the pixel value in the digital images actually are non-linear mapping of the irradiation of scene, it is impossible for normal intra-oral cameras with single exposure to provide dynamic range high enough to describe the whole irradiation of scene in one image (shown in FIG. 1(c)). So it's unavoidable to map high-light regions corresponding to specular reflection into the over-saturation regions in the final digital images captured by normal camera with single exposure.

Figure 2:
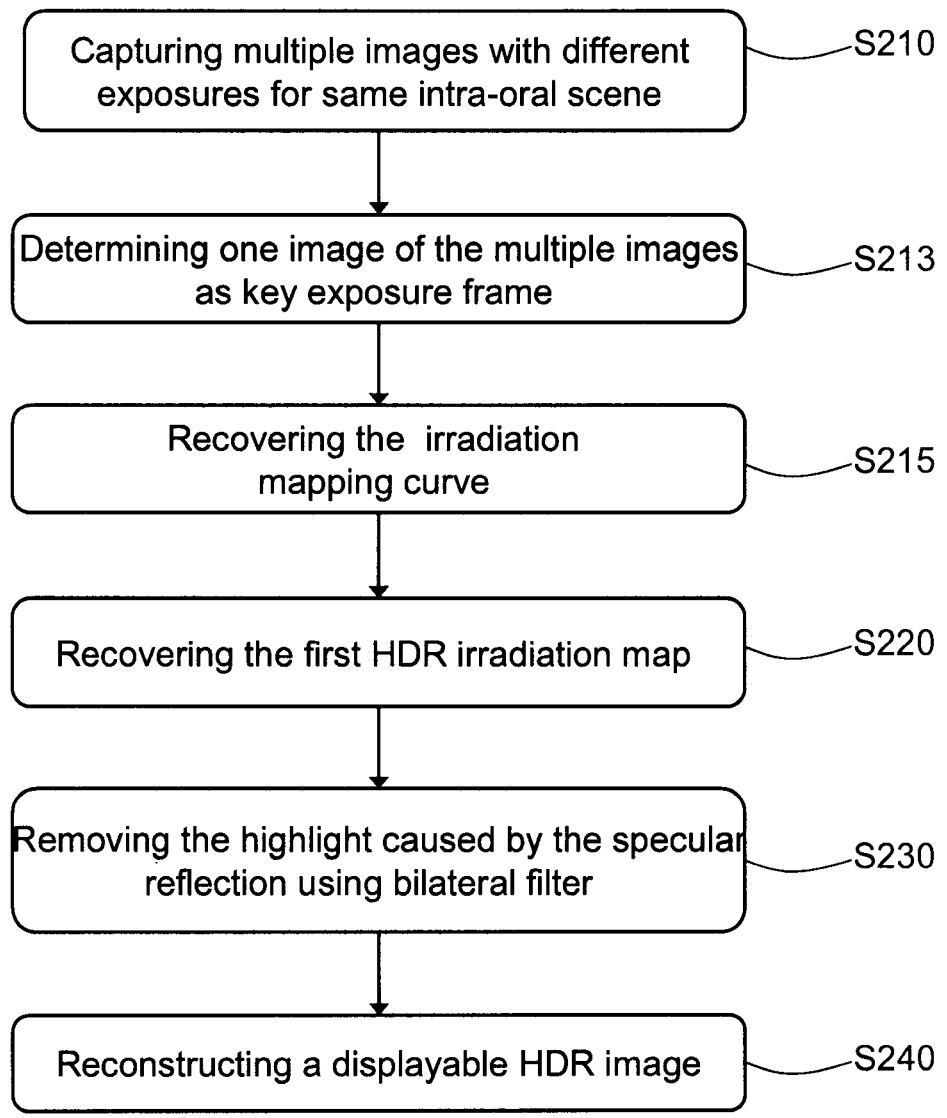
FIG. 2 is a workflow of a method for intra-oral imaging in accordance with an embodiment of the invention.
Figure 3:
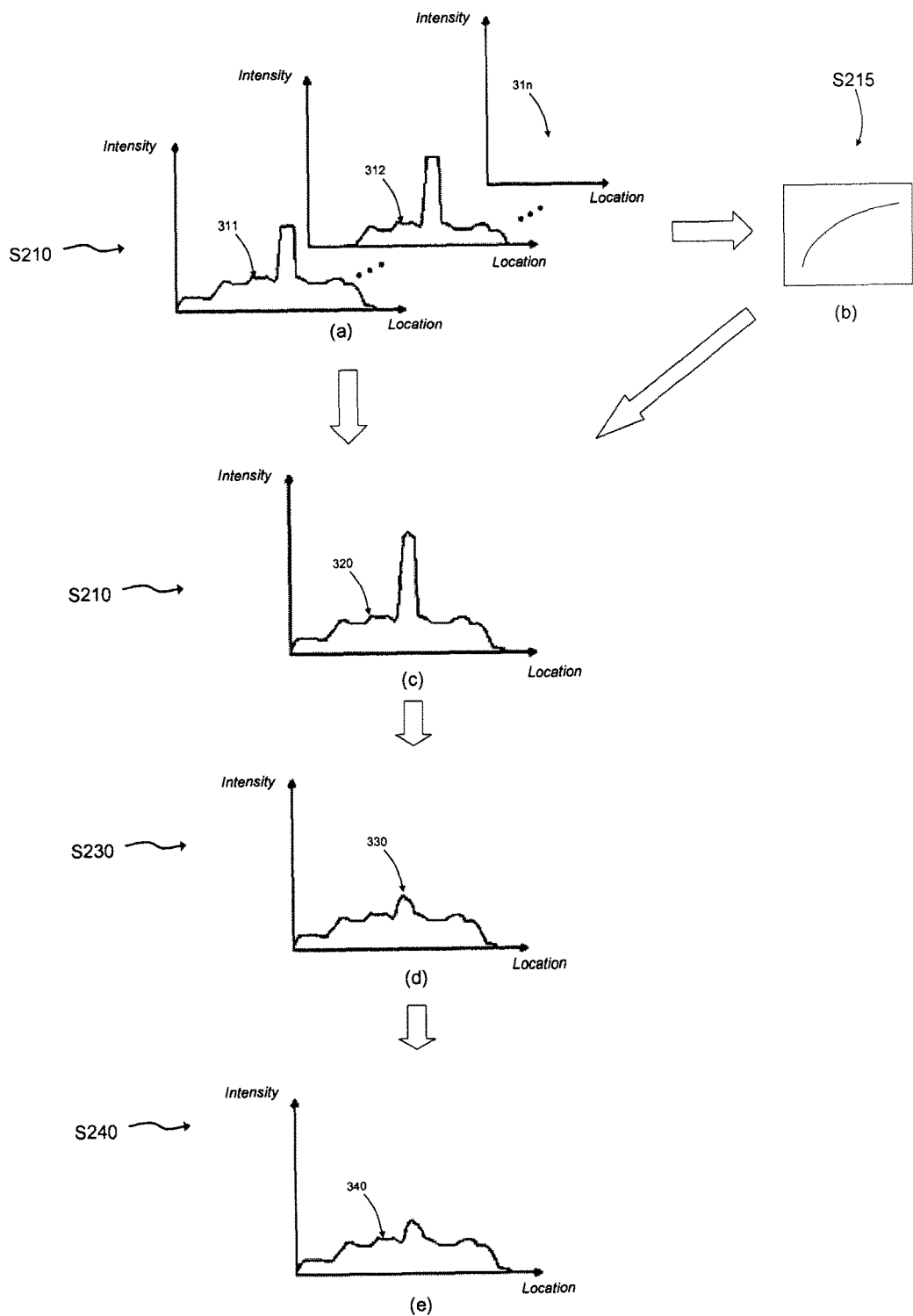
FIG. 3 shows a schematic diagram of intra-oral imaging corresponding to the method as illustrated in FIG. 2.

An embodiment of suppressing the specular reflection is provided as illustrated in FIGS. 2 and 3. Meanwhile, it also discloses a method for intra-oral imaging correspondingly, according to which a HDR image without over-saturated highlight region can be finally generated in real-time. Thus, the teeth can be clearly shown in a 2D HDR image, which would great contributes to the diagnosis of the oral cavity. The method is described in detail as follows based on FIGS. 2 and 3.

In the step of S210, a series of images as shown in FIG. 3(a) is captured by an intra-oral camera with different exposures.

In this embodiment, when an intra-oral camera is used to observe a scene including teeth at least, its illuminator can, but not limit to, be white-light, such as LEDs. The intra-oral camera projects the light from the illuminator onto the scene and then images the reflected light. As an illustrated example, the intra-oral camera can refer to a published patent, i.e., Application No. US2010/0268069 to Rongguang Liang, "Dental Surface Imaging Using Polarized Fringe Projection", whose entire contents are incorporated by reference herein.

The intra-oral camera is also configured as adjustable for exposure when capturing images. In this embodiment, each exposure corresponding to a respective image can be determined by its corresponding exposure duration. Of course, other way can be used to identify each exposure when capturing image. A plurality of images, with number of n, i.e., 311, 312 to 31n, can be captured for the same scene with n increasing exposure durations. Alternatively, the number of n can be set as 4, 8 or 16. The more images captured, more clear the HDR image finally shows. Meanwhile, the range of all these exposures takes affect on the clearness of the final HDR image, and it can be determined by an embodied intensity of the specular reflection.

It is also noted that, in the process of capturing a series of images as shown in FIG. 3(a), all parameters except exposure are unchangeable, and the intra-oral camera also keeps static all the time over the oral cavity. Therefore, the scene for multiple imaging can be regarded as a static scene.

Further, in the step of S213, one of the multiple images is determined as a key exposure frame.

In this embodiment, comparing all exposures of the multiple images with the average value of the all exposures, the one with exposure closest to the average value is determined as the key exposure frame. Namely, the exposure duration of the key exposure frame is closed to the average automatic exposure of same intra-oral camera under same illumination in intra-oral environments.

Moreover, the key exposure frame looks closely like a normally auto-exposed image, in which different regions, such as teeth region, gum region and background, can segmented by an well-known iterative adaptive threshold calculation procedure. As a particular example of the color segmentation, the adaptive threshold segmentation can be carried out on an image of Red component/Green component, by which teeth region can be segmented out. Therefore, the over-saturated high-light regions under over-exposuring can be determined and extracted from the key exposure frame. Likely, other regions that the user intends to observe, such as teeth region and gum region, can also be determined and extracted from the key exposure frame in same way.

Further, in the step of S215, a irradiation mapping curve shown in FIG. 3(b) is recovered basing on the multiple images shown in FIG. 3(a)

In this embodiment, to recover the irradiation mapping curve, if all pixels in the images with different exposure durations would contribute the statistic optimal solution given the recovery optimization equation, this will introduce huge computation. Thus, it's almost impossible to implement in real-time, but actually the homogeneous pixels corresponding same materials contribute similarly to the optimal solution and thus, many pixels marginally contribute. Namely, the result of calculation involving all pixels in the whole homogeneous region is similar with the result of calculation involving a few representative pixels of the whole homogeneous region. Thereby, it's enough to involve fewer pixels in the whole homogeneous region to compute the curve.

In order to recover the irradiation mapping curve in real-time, the teeth regions, gum regions and highlight regions can be segmented in the key exposure frame described in the step of 213, and the pixels in teeth regions, gum regions and highlight regions can be extracts respectively.

Thus, many fewer pixels (e.g., teeth, gum and highlight regions) will be employed to solve the equation and recover the irradiation mapping curve while similar results can be obtained. Thus, recovering of the irradiation mapping curve in real-time is possible. Moreover, to ensure the involved calculation is real-time, a shape-based spatial adaptive down-sample method can be used, since it's not necessary to involve all pixels in the mapping curve calculation, and some representative pixels in each regions of the teeth regions, gum regions and highlight regions can provide accurate enough calculation. In the shape-based spatial adaptive down-sample method, the areas of different segmented regions are calculated firstly; and then, for each separate region, a down-sample rate and a relevant down-sample mesh is generated so as to make each segmented region provide equal number of pixels. Therefore, it is easy to provide high computational efficiency and high accuracy of the reconstructed curve of whole scene, and the irradiation mapping curve can be recovered in real-time.

Further, in the step of S220, the first HDR irradiation map shown in FIG. 3(c) is recovered according to the multiple images shown in FIG. 3(a) and the irradiation mapping curve shown in FIG. 3(b).

In this embodiment, firstly, for every one of the multiple images, each pixel value is mapped into an irradiation value according to the irradiation mapping curve. Then, the first HDR irradiation map can be recovered and obtained by weighted averaging the irradiation values of all of the multiple images for every pixel. The first HDR irradiation map shown in FIG. 3(c) can represent a summarization of the diffusion reflection and the specular reflection, thus, it is basically equate to the original irradiation map as shown in FIG. 1(b). In this way, by multiple-exposure, the actual inputting irradiation of the intra-oral camera can be basically obtained and embodied in the first HDR irradiation map.

The above steps of recovering the first HDR irradiation map are illustrated in detail as follows.

In the recovered irradiation color image, specular regions appear high-light where irradiation intensity values are composed of 2 components including diffusing component and specular reflection component, which means that the pixel value $\dot{I}(x,y)=[I_R(x,y), I_G(x,y), I_B(x,y)]$ at location $(x,y)$ in the reflected light color image captured by a RGB camera can be represented as the linear combination of the diffuse color component $\dot{I}^D(x,y)=[I_R^D(x,y), I_G^D(x,y), I_B^D(x,y)]$ and the specular color component $\dot{I}^S(x,y)=[I_R^S(x,y), I_G^S(x,y), I_B^S(x,y)]$; wherein $(x, y)$ representing spatial location of pixel, given white-light as illumination source. Wherein, the $\dot{I}(x,y)$ is the pixel value, $I_R(x, y)$ is a pixel value of red component, $I_G(x, y)$ is a pixel value of green component, $I_B(x, y)$ is a pixel value of red component; $\dot{I}^D(x,y)$ is the diffuse color component, $I_R^D(x,y)$ is a pixel value of the diffuse red component, $I_G^D(x,y)$ is a pixel value of the diffuse green component, $I_B^D(x,y)$ is a pixel value of the diffuse blue component; $\dot{I}^S(x,y)$ is the specular color component, $I_R^S(x,y)$ is a pixel value of the specular red component, $I_G^S(x,y)$ is a pixel value of the specular green component, $I_B^S(x,y)$ is a pixel value of the specular blue component.

High-light removal techniques will estimate the diffusion color component from color component in the recovered irradiation color image. The diffuse chromaticity can be calculated by the formula (1) below.

$$\theta(x, y) = [\theta_R(x, y), \theta_G(x, y), \theta_B(x, y)] \quad (1)$$

$$= \begin{bmatrix} \dfrac{I_R^D(x, y)}{I_R^D(x, y) + I_G^D(x, y) + I_B^D(x, y)}, \\ \dfrac{I_G^D(x, y)}{I_R^D(x, y) + I_G^D(x, y) + I_B^D(x, y)}, \\ \dfrac{I_B^D(x, y)}{I_R^D(x, y) + I_G^D(x, y) + I_B^D(x, y)} \end{bmatrix}$$

Wherein, $\theta(x,y)$ is the diffuse chromaticity, $\theta_R(x,y)$ is the diffuse chromaticity of red component, $\theta_G(x,y)$ is the diffuse chromaticity of green component, $\theta_S(x,y)$ is the diffuse chromaticity of blue component.

The maximum diffuse chromaticity can be calculated by the formula (2) below:

$$\theta_{max}(x,y) = \max\,[\theta_R(x,y), \theta_G(x,y), \theta_B(x,y)] \quad (2).$$

Wherein $\theta_{max}(x,y)$ is the maximum diffuse chromaticity.

Moreover, there is an empirical formulation (3) to estimate the diffusion color component for each pixel.

$$\begin{bmatrix} I_R^D(x, y) \\ I_G^D(x, y) \\ I_B^D(x, y) \end{bmatrix} = \begin{bmatrix} I_R(x, y) - \dfrac{\max[I_R(x, y), I_G(x, y), I_B(x, y)] - \theta_{max}(x, y)[I_R(x, y) + I_G(x, y) + I_B(x, y)]}{1 - 3 \cdot \theta_{max}(x, y)} \\ I_G(x, y) - \dfrac{\max[I_R(x, y), I_G(x, y), I_B(x, y)] - \theta_{max}(x, y)[I_R(x, y) + I_G(x, y) + I_B(x, y)]}{1 - 3 \cdot \theta_{max}(x, y)} \\ I_B(x, y) - \dfrac{\max[I_R(x, y), I_G(x, y), I_B(x, y)] - \theta_{max}(x, y)[I_R(x, y) + I_G(x, y) + I_B(x, y)]}{1 - 3 \cdot \theta_{max}(x, y)} \end{bmatrix} \quad (3)$$

In small local regions where color are consistent, $\theta_{max}(x,y)$ of each pixel varies very little, but for the specular pixels, the specular reflection results in color discontinuities in the local region with same surface color, and detail-preserved filter including famous bi-lateral filter can be used to remove the local discontinuities.

Further, in the step of S230, the highlight caused by the specular reflection is removed from the first HDR irradiation map using bilateral filter so as to obtain a second HDR irradiation map.

In this embodiment, in aforesaid contents, the teeth region, gum region and highlight region can be segmented in the key exposure frame, especially for each highlight region, it can be extracted from the key exposure frame. After determination of the maximum geometric size of the highlight regions (i.e., the maximum distance from boundary to mid-axis of the highlight regions), this maximum geometric size can be set as scale parameter of bilateral filter; then, the bilateral filter is run repeatedly on the $\theta_{max}(x, y)$ of the first HDR irradiation map until the criteria of minimum change is reached. Basing on the criteria of minimum change, it is easy to remove any specular reflection that appears discontinuous and abrupt. Thus, the over over-saturated highlight regions can be removed from the first HDR irradiation map, and it succeed to obtain the second HDR irradiation map shown in FIG. 3(d) in which the specular reflection is greatly suppressed and the details corresponding to the diffusion reflection are completely reserved.

Thus, the filter used in the step of S230 is not confined to the bilateral filter in the above embodiment, and any other detail-reserved filtering technology can be applied herein for removing highlight. When using detail-reserved filter, a details smaller than the criteria of minimum change can be successfully remained while the highlight larger than the criteria of minimum change can be removed easily.

So far, the specular reflection is removed while the diffuse reflection is remained in second HDR irradiation map of the intra-oral scene.

Further, in the step of S240, to display the HDR image on the low dynamic range displaying device, a displayable HDR image shown in FIG. 3(e) is reconstructed using tone mapping for the second HDR irradiation map.

In this embodiment, to reconstruct the final white-light image that can be displayed in a digital display with low dynamic range, tone mapping is used to map the high dynamic range irradiation value into the normal image dynamic range. Further, the maximum geometric size of teeth region extracted in the key exposure frame, which is defined as a maximum distance from boundary to mid-axis if the teeth region, is used as a scale parameter of another bilateral filter, and this bilateral filter is used to discompose the second HDR irradiation map into the coarse level and the fine level. Since the coarse level dominants the main dynamic range, it should be down-scaled so as to make the dynamic range suitable to reconstruct the normal image. After similar operations on the fine level, the scaled coarse and fine level is combined together to generate a final teeth image that can be conveniently observed by dentist.

Finally, the HDR teeth images, in which brighten and darken objects are clearly captured simultaneously, are obtained with specular reflection being greatly suppressed.

It can be understood that, in the other embodiment, in case that the second HDR irradiation map could be directly displayed in a display adapted to display any HDR irradiation map, the step of S240 can be omitted.

Having described preferred embodiments of the invention, it will now become apparent to those of ordinary skill in the art that other embodiments incorporating these may be used. Additionally, the software included as part of the invention may be embodied in a computer program product that includes a computer useable medium. For example, such a computer usable medium can include a readable memory device, such a hard drive device, a CD-ROM, a DVD-ROM, or a computer diskette, having computer readable program code segments stored thereon. The computer readable medium can also include a communications link, either optical, wired, or wireless, having program code segments carried thereon as digital or analog signals. Accordingly, it is submitted that the invention should not be limited to the described embodiments but rather should be limited only by the spirit and scope of the appended claims. All publish and references cited herein are expressly incorporated herein by reference in their entirety.

What is claimed is:

1. A method for intra-oral imaging, comprising:
  capturing, with an intra-oral camera, multiple images with different exposures for an intra-oral (IO) scene:
  generating, using a processor, a first High Dynamic Range (HDR) irradiation map of teeth with multiple images captured with different exposures for the IO scene by;
    receiving the multiple images with different exposures for the IO scene;
    determining one image of the multiple images with different exposures for the IO scene as a key exposure frame;
    extracting teeth regions, gum regions, and highlight regions in the key frame;
    comparing the multiple images with different exposures for the same intra-oral scene to generate an irradiation mapping curve for the IO scene; and
    transforming at least the key exposure frame into the first HDR irradiation map by mapping pixel values into irradiation values for The extracted teeth regions, the extracted gum regions, and the extracted the highlight regions of the key exposure frame by weighted averaging based on the irradiation mapping curve for the IO scene;
  reducing, using a second processor, highlight caused by a specular reflection from the first HDR irradiation map so as to obtain a second HDR irradiation map in which the specular reflection is at least partly suppressed by filtering local abrupt discontinuities within a single color consistent local region of the first HDR irradiation map; and
  reconstructing, using a third processor, a displayable HDR image based on the second HDR irradiation map.

2. The method of claim 1, wherein the determining one image of the multiple images with different exposures for the IO scene as key exposure frame comprises comparing exposures of the multiple images with the average value of all exposures of the multiple images, and an exposure closest to the average value is determined as the key exposure frame.

3. The method of claim 1, wherein the reducing highlight caused by the specular reflection is done in a detail-preserved way using a bilateral filter, where the first processor, the second processor and the third processor are the same processor.

4. The method of claim 3, wherein the step of reducing highlight includes determination of the scale parameters of the bilateral filter using the key exposure frame, where the first processor, the second processor and the third processor are different processors.

5. The method of claim 4, wherein an over-saturated highlight region is segmented and extracted from the key exposure frame.

6. The method of claim 5, wherein a maximum geometric size of the over-saturated highlight region is set as a scale parameter of the bilateral filter, where two of the first processor, the second processor and the third processor are the same processor.

7. The method of claim 1, wherein a shape-based spatial adaptive down-sample method is used for reducing the computation of recovering the irradiation mapping curve, wherein the shape-based spatial adaptive down-sample method comprises the steps of:
  calculating the areas of each segmented region of the teeth region, gum region and highlight region; and
  generating a down-sample rate and a down-sample mesh so as to make each segmented region provide an equal number of pixels.

8. The method of claim 1, wherein the displayable HDR image is displayed in real-time.

9. The method of claim 1, wherein the
reconstructing the displayable HDR image based on the second HDR irradiation map uses tone mapping so as to display the HDR image onto a low dynamic range displaying device.

10. A system for intra-oral imaging, comprising:
an intraoral camera to generate a first High Dynamic Range (HDR) irradiation map of teeth with multiple images captured with different exposures for same intra-oral scene,
where the intraoral camera comprises means for determining one image of the multiple images as a key exposure frame, for recovering an irradiation mapping curve based on the multiple images with the different exposures for the same intra-oral scene, and for obtaining the first HDR irradiation map based on the key exposure frame and the irradiation mapping curve by mapping pixel values into irradiation values on the first HDR irradiation map for said key exposure frame by weighted averaging based on the irradiation mapping curve;
a filter to remove highlight caused by a specular reflection from local abrupt discontinuities within a single color consistent local region of the first HDR irradiation map so as to obtain a second HDR irradiation map in which the specular reflection is at least partly suppressed; and
a processor, in communication with one of the intraoral camera or the filter, configured to reconstruct a displayable HDR image based on the second HDR irradiation map.

11. The system of claim 10, wherein the determining one image of the multiple images with different exposures for the IO scene as key exposure frame comprises comparing exposures of the multiple images with the average value of all exposures of the multiple images, and an exposure closest to the average value is determined as the key exposure frame.

12. The system of claim 10, wherein the filter is a detail-preserved filter, and wherein the detail-preserved filter is a bilateral filter.

13. The system of claim 10, wherein a shape-based spatial adaptive down-sample method is used for reducing the computation of recovering the irradiation mapping curve, wherein the shape-based spatial adaptive down-sample method comprises the steps of:
calculating the areas of each segmented region of the teeth region, gum region and highlight region; and
generating a down-sample rate and a relevant down-sample mesh so as to make each segmented region provide an equal number of pixels.

14. The system of claim 10, where teeth regions, gum regions, highlight regions and background are segmented in the key exposure frame, and the teeth regions, gum regions and highlight regions are extracted from the key exposure frame so that the pixels corresponding to the teeth regions, gum regions and highlight regions are employed to recover the irradiation mapping curve.

15. A non-transitory computer-readable storage medium, storing program instructions computer-executable on a computer to perform operations comprising:
generating a first High Dynamic Range (HDR) irradiation map of teeth with multiple images captured with different exposures for an intra-oral scene, where generating the first HDR irradiation map includes:
receiving the multiple images with different exposures for the intra-oral scene;
determining one image of the multiple images with different exposures for the same intra-oral scene as key exposure frame;
segmenting at least the key exposure frame into teeth regions, gum regions, highlight regions and background;
down-sampling the teeth regions, the gum regions, and the highlight regions to select representative pixels in the key frame;
comparing down-sampled representative pixels from each of the multiple images with different exposures for the same intra-oral scene to generate an irradiation mapping curve for the intra-oral scene;
transforming at least the key exposure frame into the first HDR irradiation map by mapping the pixel value into irradiation value for every pixel of the key exposure frame by weighted averaging based on the irradiation mapping curve for the intra-oral scene; and
reconstructing a displayable HDR image based on the first HDR irradiation map.

* * * * *